US00PP34009P2

(12) United States Plant Patent
Moon

(10) Patent No.: US PP34,009 P2
(45) Date of Patent: Mar. 15, 2022

(54) ***TAXODIUM* PLANT NAMED 'TDMTF'**

(50) Latin Name: *Taxodium distichum*
Varietal Denomination: TDMTF

(71) Applicant: Dwayne Moon, Washington, GA (US)

(72) Inventor: Dwayne Moon, Washington, GA (US)

( * ) Notice: Subject to any disclaimer, the term of this patent is extended or adjusted under 35 U.S.C. 154(b) by 0 days.

(21) Appl. No.: 17/235,677

(22) Filed: Apr. 20, 2021

(51) Int. Cl.
*A01H 7/00* (2006.01)
*A01H 6/00* (2018.01)

(52) U.S. Cl.
USPC ..... Plt./213
CPC ..... *A01H 6/00* (2018.05)

(58) Field of Classification Search
USPC ..... Plt./213
CPC ..... A01H 7/00; A01H 5/00
See application file for complete search history.

*Primary Examiner* — Kent L Bell
(74) *Attorney, Agent, or Firm* — Cassandra Bright

(57) ABSTRACT

A new and distinct *Taxodium* cultivar named 'TDMTF' is disclosed, characterized by an upright habit and feather-like foliage which is closely spaced. Fall foliage color is orange. The new cultivar is a *Taxodium*, suitable for ornamental garden purposes.

2 Drawing Sheets

Figure 1:
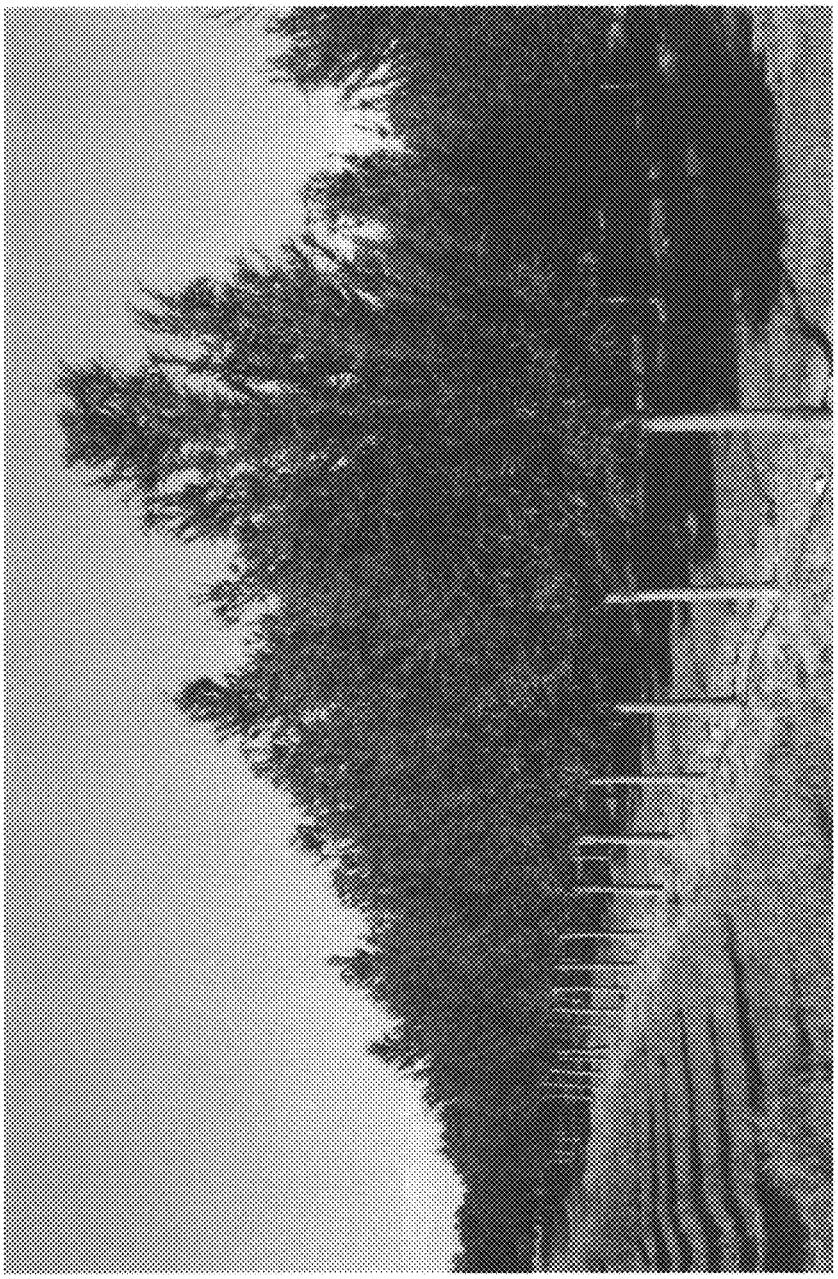

Latin name of the genus and species: *Taxodium distichum.*
Variety denomination: 'TDMTF'.

BACKGROUND OF THE INVENTION

The new cultivar is a product of a planned breeding program. The new variety was discovered growing as a seedling among a group of crossbred *Taxodium distichum* trees at a tree farm in Washington, Ga. The inventor made this discovery in the Summer of 2014. The exact seed and pollen parents cannot be identified.

After identifying the new variety as a potentially interesting selection during 2014, the inventor first organized propagation of 'TDMTF' by softwood cuttings at the same commercial nursery during 2014. The inventor continued controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'TDMTF' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TDMTF'. These characteristics in combination distinguish 'TDMTF' as a new and distinct *Taxodium* cultivar:

1. Tight, dense habit with feather-like needles closely spaced
2. Orange color in fall
3. Upright, fastigiate growth
4. Dark green foliage

COMPARISON TO PARENT VARIETY

The exact parent varieties cannot be identified.

COMMERCIAL COMPARISON

*Taxodium* 'TDMTF' can be compared to the commercial variety *Taxodium distichum* 'Sofine', U.S. Plant Pat. No. 13,431 Plants are similar in most horticultural characteristics, however, plants of the new variety differ in the following:

1. 'TDMTF' is more upright in growth habit and structure than this comparator.
2. 'TDMTF' forms finer, denser foliage.
3. The new variety produces a different orange Fall foliage color.
4. The new variety grows slightly slower than this comparator.

*Taxodium* 'TDMTF' can be compared to the commercial variety *Taxodium distichum* 'Nelson', U.S. Plant Pat. No. 12,502. Plants are similar in most horticultural characteristics, however, plants of the new variety differ in the following:

1. 'TDMTF' is more upright in growth habit and structure than this comparator.
2. 'TDMTF' forms finer, denser foliage.
3. The new variety produces a different orange Fall foliage color.
4. The new variety grows slightly slower than this comparator.

*Taxodium* 'TDMTF' can be compared to the commercial variety *Taxodium distichum* 'Peve Minaret' (unpatented). Plants are similar in most horticultural characteristics, however, plants of the new variety differ in the following:

1. 'TDMTF' grows larger than this comparator, which grows into a small tree with a very enlarged trunk.
2. 'TDMTF' grows faster than this comparator.

BRIEF DESCRIPTION OF THE PHOTOGRAPHS

The accompanying photograph in FIG. 1 illustrates in full color typical trees of 'TDMTF' grown outdoors in Washington, Ga. The trees are approximately 3 years old, shown growing in the ground.

Figure 2:
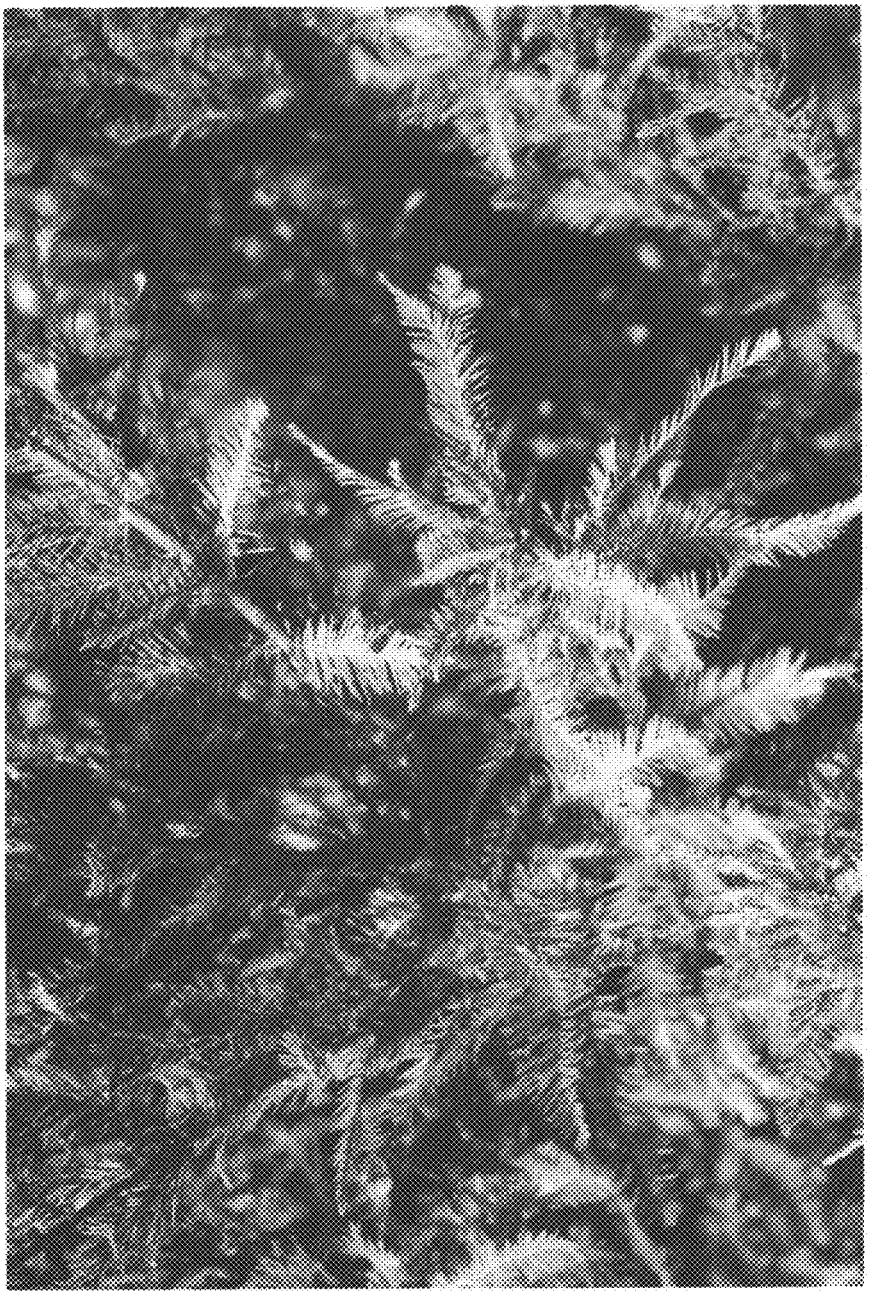

FIG. 2 illustrates a close up of typical foliage of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'TDMTF' plants grown outdoors in Loganville, Ga. Plants are approximately 2-3 years old, in a 3 gallon nursery container. Measurements and numerical values represent averages of typical plant types.

Botanical classification: *Taxodium distichum* 'TDMTF'.

PLANT

Growth habit: Upright deciduous, coniferous tree.
Height: About 10 feet at 3 years.
Plant spread: About 4 feet at 3 years.
Typical growth rate: Moderate to rapid.
Trunk characteristics:
- *Diameter*.—About 3.5 inches measured at approximately 3 inches above soil level at 3 years.
- *Color*.—Near RHS Greyed-Green 197D and 198A with vertical striations near 197A.
- *Surface texture*.—Striated, furrows immature, bark not yet fully formed, not yet peeling.

Main stem:
- *Diameter*.—About 2 inches measured at the level of branching, at 3.5 years.
- *Shape*.—Round.
- *Length*.—About 5 to 7 feet at about 3.5 years.
- *Internode length*.—Average range 5 to 12 cm.
- *Color*.—Young: Near RHS Greyed-Red 178B. Mature: Near RHS Greyed-Green 198B.
- *Surface texture*.—Scaly.

Branching habit: Acute, 15 to 45 degrees from center.
Length of lateral branches: About 30 to 90 cm.
Average number of lateral branches: About 30.
Diameter of lateral branches: About 20 mm.
Lateral branch color: Near RHS Greyed-Orange 177A, younger branches near Greyed-Orange 176A.
Lateral branch strength: Strong.
Lateral branch scales:
- *Shape*.—Awl-shaped.
- *Length*.—Average range 8 to 17 mm.
- *Width*.—Average range 5 to 9 mm.
- *Texture*.—Rough, slightly sharp.
- *Color*.—Near RHS Greyed-Orange 177D.

FOLIAGE

Leaf:
- *General description*.—Soft, feathery and dense. No prickles and no spines.
- *Arrangement*.—Pinnate, sub-opposite foliage.
- *Shape*.—Lanceolate.
- *Average length*.—5 to 8 cm.
- *Average width*.—2.4 to 3 cm.
- *Attachment*.—Sessile.
- *Pinnae per leaf*.—Average range 50 to 80.
- *Fragrance*.—Weak.

Pinnae:
- *Shape*.—Linear.
- *Average length*.—10 to 15 mm.
- *Average width*.—1 to 1.5 mm.
- *Attachment*.—Sessile.
- *Apex*.—Rounded.
- *Base*.—Truncate.
- *Margin*.—Entire.
- *Texture of top surface*.—Glabrous.
- *Texture of bottom surface*.—Glabrous.
- *Color*.—Young foliage upper side: Near RHS Green 139C. Young foliage under side: Near RHS Green 139C. Mature foliage upper side: Near RHS Green 137D. Mature foliage under side: Near RHS Green 137D. Fall foliage upper side: Near RHS Greyed-Orange N172A flushed N172C. Fall foliage under side: Near RHS Greyed-Orange N172A flushed N172C.
- *Venation*.—Indistinguishable from leaf blade.

FLOWER

Monoecious, borne on pendulous panicles, of about 200 to 300 during Spring. Immature floral structures colored near Yellow-Green N144A, maturing to Grey-Brown 199A.

OTHER CHARACTERISTICS

Cones/strobili: Female cones globular, deeply and irregularly ridged, about 2 to 2.5 cm in diameter. Colored near Green 138C, maturing to Grey-Brown 199A. Seeds flat, irregular deltate, colored near Brown 200B. Average 15 scales per cone.

Disease and pest resistance: Neither resistance or susceptibility to normal diseases and pests of *Taxodium distichum* observed.

Drought tolerance: No tolerance for drought observed. *Taxodium distichum* can be moderately drought tolerant once established. Wet soils well tolerated.

Temperature tolerance: USDA Zones 5-9.

What is claimed is:

1. A new and distinct cultivar of *Taxodium* plant named 'TDMTF' as herein illustrated and described.

* * * * *